United States Patent [19]

Sarangapani

[11] Patent Number: 5,328,954

[45] Date of Patent: Jul. 12, 1994

US005328954A

[54] ENCRUSTING AND BACTERIAL RESISTANT COATINGS FOR MEDICAL APPLICATIONS

[75] Inventor: Shantha Sarangapani, Walpole, Mass.

[73] Assignee: ICET, Inc., Norwood, Mass.

[21] Appl. No.: 48,489

[22] Filed: Apr. 16, 1993

[51] Int. Cl.⁵ ............................................. C08L 75/00
[52] U.S. Cl. ................................ 524/589; 524/590;
524/871; 524/874; 523/105; 523/106;
428/423.1
[58] Field of Search ............... 524/589, 590, 871, 874;
523/105, 106; 428/423.1

[56] References Cited

U.S. PATENT DOCUMENTS 4,946,449 11/1989 Davis ................................. 524/589

*Primary Examiner*—Maurice J. Welsh
*Attorney, Agent, or Firm*—Hale and Dorr

[57] ABSTRACT

Disclosed is an encrustation and bacterial-resistant coating for use on medical devices and in other medical-related applications. The coating includes a reaction product formed by the covalent linkage of a hydrophilic polyurethane prepolymer and aminopolycarboxylic acid. A urease inhibitor and/or an antibacterial agent may also be added to the coating.

28 Claims, 9 Drawing Sheets

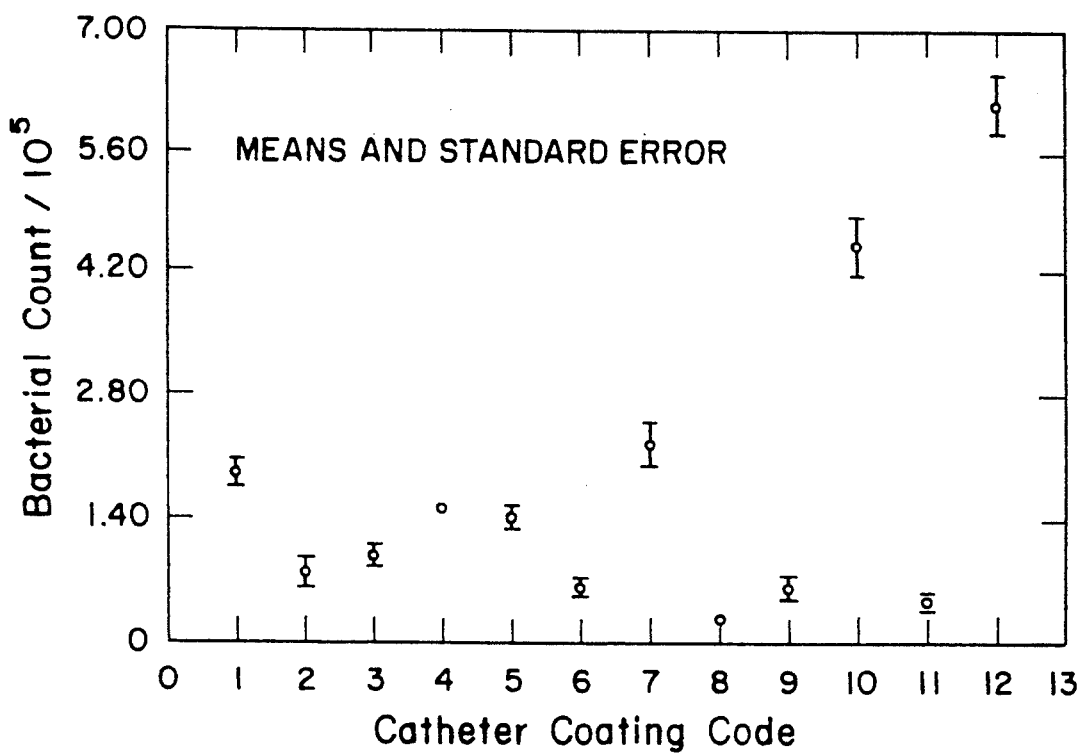
FIG. 5 P. MIRABALIS ADHERENCE TO CATHETERS ALL DATA, INC. SILICONE AND TEFLON

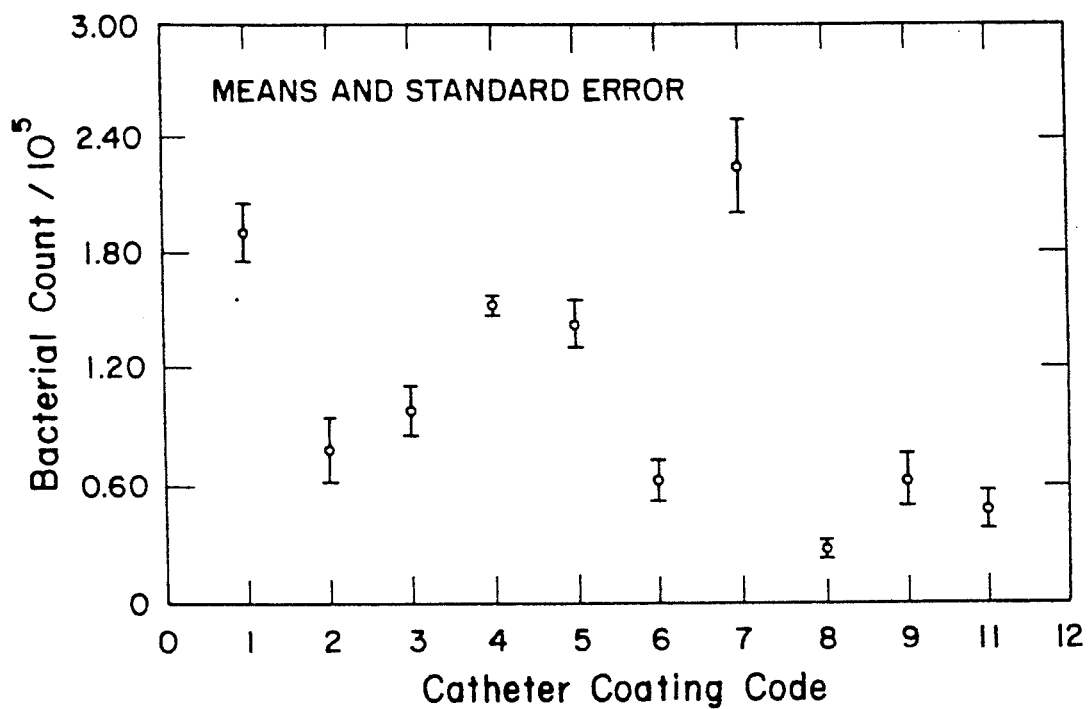
FIG. 6 P. MIRABALIS ADHERENCE TO CATHETERS ICT COATINGS ONLY

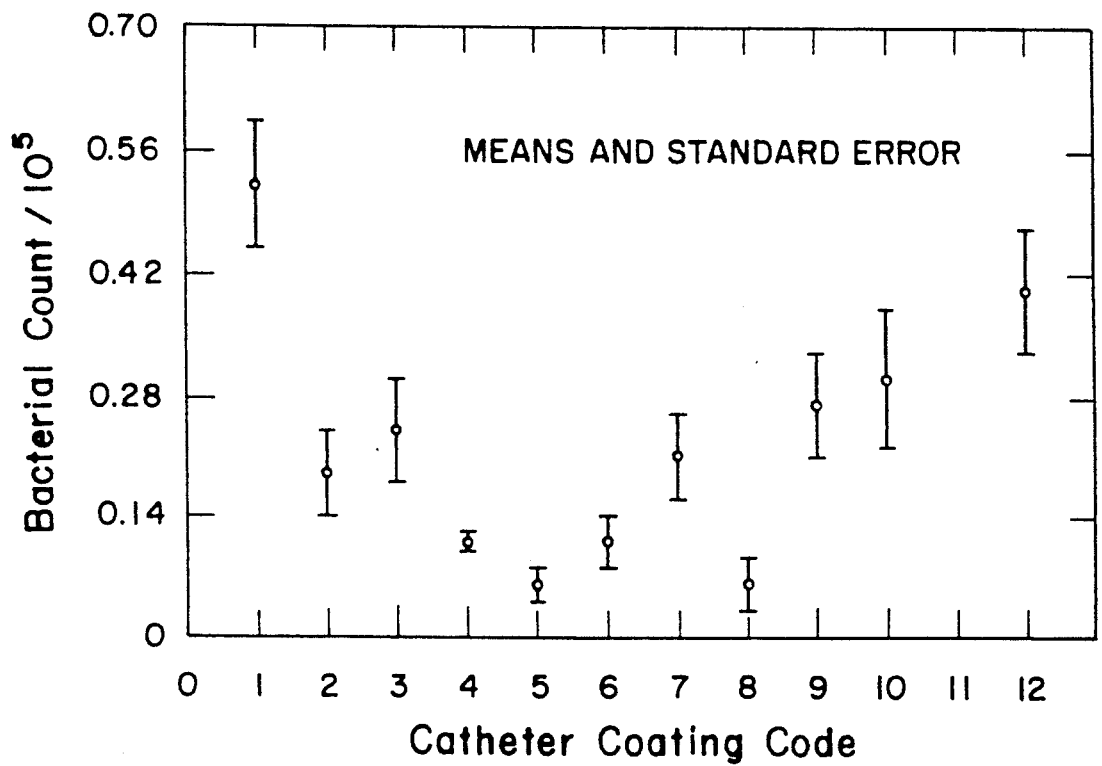
FIG. 7 P. VULGARIS ADHESION TO CATHETERS ALL DATA, INC. SILCONE AND TEFLON

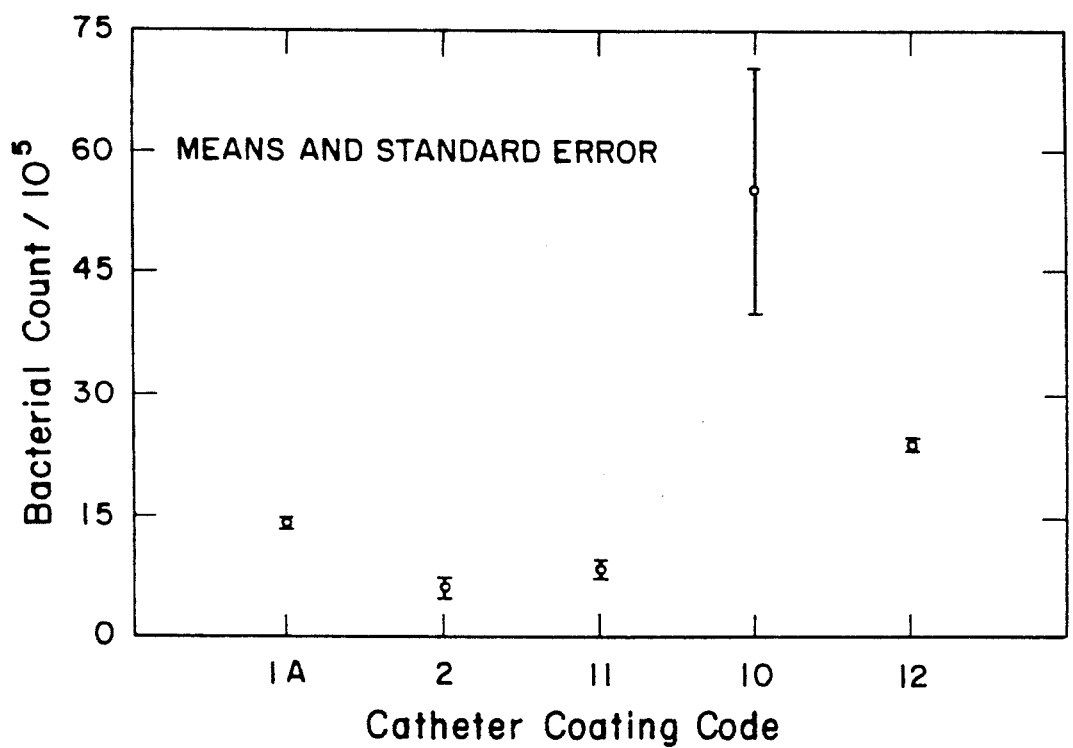
FIG. 8 P. MIRABALIS ADHERENCE TO CATHETERS SECOND DATA SET

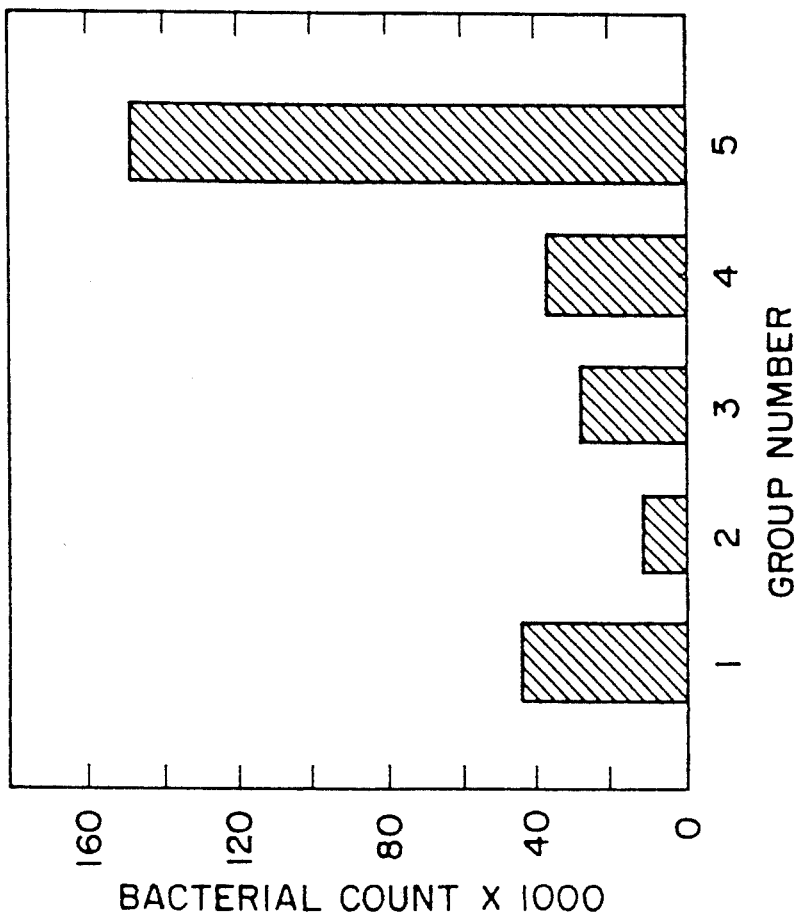

ENCRUSTING AND BACTERIAL RESISTANT COATINGS FOR MEDICAL APPLICATIONS

This invention has been developed in part with funding provided by the National Institute of Health pursuant to NIH SBIR Phase I Grant R43DK43589-01.

BACKGROUND OF THE INVENTION

This invention relates to medical devices that are resistant to bacterial growth or encrustation such as a) urinary catheters and more particularly to urinary catheters constructed of a material which enables the urinary catheters to inhibit urease and to prevent calcium and magnesium phosphate deposits on the catheters and b) contact lenses, more particularly to extended wear lenses coated with a suitable material to enable the lenses to resist the adherence of microorganisms.

Urinary Catheters: Catheters are used in urological surgery and when other methods of managing urinary incontinence fail. These catheters are generally made from a nontoxic, non-irritating material which is flexible but which will withstand collapse. Ideally they should resist colonization by bacteria and encrustation by mineral deposits.

The most common materials used for the catheters are latex, plastic or silicone. All biomaterials, including the most recently tested polyurethane, polyurethane-carbon and silicone-carbon, become encrusted with mineral deposits to varying extents. The degree of encrustation formation on biomaterials exposed to urine is dependent upon the biomaterial, the length of urinary exposure, the presence of infection and the solute content of urine. Several independent studies (e.g. Hukins et al., 1989) of the scraped encrusted material have identified - two major salts, namely apatite $Ca_5(PO_4)_3(OH)$ and struvite $Mg\ NH_4PO_4\ 6H_2O$. A very small amount of brushite $CaHPO_4.2H_2O$ has also been identified. Apatite is precipitated from urine under alkaline conditions (pH=9.2) along with struvite. Brushite with a $K_{sp}$ of the order of $10^{-5}$ is not stable above pH=7; but is precipitated below 6.5.

The pH increase of urine occurs due to urease producing bacteria, that infect the urine. Urease catalyzes the hydrolysis of urea at an enormous rate ($10^{14}$ times as fast as the spontaneous hydrolysis of urea which is not observable in neutral solution) producing ammonia, which in turn precipitates calcium phosphates.

Microbial heterogeneity and structural complexity of the biofilms observed on infected catheter materials by means of scanning and transmission electron microscopy reveal a variety of microflora. It appears that the adherent microcolonies of bacteria are much less susceptible than their planktonic counterparts to antibiotics because the extensive anionic matrix surrounding the cell appears to comprise an ion exchange barrier between charged antibiotic molecules and their cellular targets. Antibiotics should be reserved for symptomatic, febrile infections; otherwise their use produces a change in bacterial flora with the potential for producing resistance.

Bacteriurea in a catheterized patient indicates the urinary tract has become colonized or infected. Administration of anti-bacterials such as nitrofurantoin, methenamine, and naldixic acid are used in practice. Most of these are not very effective in alkaline urine, and to achieve a high concentration in urine, the patient has to be given enormous doses.

Catheter associated bacteriurea results from ascending bacterial colonization within glycocalyx enclosed biofilm on the inside and/or outside surfaces of the catheter and drainage systems. Urinary tract catheters made from a biomaterial that inhibits bacterial adherence and thus retards upstream colonization of bacteria may reduce acquired urinary tract infection (UTI). While hydrophilic surfaces show reduced protein adhesion, antibacterial surfaces offer better protection. Either a controlled release or an antibacterial immobilized on the surface should offer continuous protection against bacterial colonization. A silver oxide catheter is described in a publication by Shaeffer, A. J., Story, K. O., Johnson, S. M. in "Effect of silver oxide/Trichloroisocyanuric Acid Antimicrobial Urinary Drainage System on Catheter Associated Bactiurea", J. Urol., 39, 60 (1988). A recent clinical study on silver catheters reported by Johnson, J. R., Roberts, P. L., Olsen, R. J., Moyer, K. A., and Stanni, W. E. in "Silver Oxide Coated Catheters", J. Infect. Diseases, 162, 1145 (1990) ) indicated the prevention of UTI among women not receiving antimicrobials.

The other problem associated with catheters left in place for long periods of time is the encrustation due to the formation of calcium hydroxyapatite and struvite. Long-term urethral catheterization is frequently necessary for patients with intractable urinary incontinence or retention. This procedure is employed in as many as 16-28% of patients in various chronic care facilities. More than 50% could suffer from blockage of their catheters. This can cause incontinence due to urinary bypassing of the catheter or acute pain and discomfort associated with urinary infection. This is particularly distressing for patients being cared for in the community where professional help is not immediately available. In addition, the coarse irregular surface may result in pain and physical trauma when the catheter is removed increasing the risk of infection.

Removal of deposits by acidic solution (citric acid-magnesium oxide) has been shown to dissolve encrustation in vitro and is now used extensively in practice. Frequent irrigation could result in the damage of the mucus in the bladder.

The patent literature abounds with patents on indwelling urinary catheter systems aimed at preventing urinary tract infection. These are mechanical devices with appropriate valve fittings to keep the drainage open at the same time preventing ascending infection. U.S. Pat. Nos. 4,946,449 issued to Richard Davis and 4,878,901 issued to Hans Ernst Sachse are two typical examples. However, these do not have any prevention methods for encrustation. In general, mechanical systems are complicated and do not provide adequate protection from infection. U.S. Pat. No. 4,932,948 issued to Kernes et al., discloses the use of a funnel shaped insert at the end of the urinary catheter that serves as a reservoir to antimicrobial agents. The antimicrobial agent is simply mixed with the ethylene/vinyl acetate polymer during the fabrication of the funnel. The catheter surface itself does not carry any antimicrobial nor is it capable of preventing encrustation. U.S. Pat. No. 4,579,554 issued to Jacob Glassman discloses a design that provides for irrigation of the catheter tube. Frequent irrigation, however, could result in the damage of the mucus in the bladder.

U.S. Pat. No. 4,642,104 issued to Sakamoto et al., teaches the use of polymers carrying multicarboxyl, amino or sulfonic acid group capable of binding antibiotics through ion exchange. The ion exchange groups are chemically introduced into the molecules of the inside and outside wall of the urethral catheter by hydrolysis of certain functionalities that are present in the polymer that is coated on the surface of the catheter. Cationic antibiotics such as polymyxins or soap preparations such as benzalkonium chloride or benzethionium chloride, cyclohexidine or povidine-iodine remain on the surface due to the electrostatic binding.

U.S. Pat. No. 4,950,256 issued to Luther et al., teaches the use of an intravascular catheter comprising a cannula for insertion into a vascular system of a patient. This catheter is coated with a hydrophilic polyurethane-polyene composition for binding antithrombogenic materials and cationic polymyxin antibiotics. Luther et al., show that the absorption of the polymyxins into the hydrophilic polyurethane can be controlled by varying the initial concentrations. The authors describe this as a time release intravascular catheter. The present invention differs from that of Luther et al., by virtue of the immobilization of polymyxin through a binding action with the dianionic diaminopropanol tetraacetic acid (DPTA) groups.

Contact Lenses: Infective ulcerative keratitis is one of the most severe hazards of hydrogel extended wear soft contact lenses (SCLs). The extent of bacterial adherence varies with the nature of the base materials, protein deposits and surface charges. While the mechanism of adhesion and colonization of bacteria on SCLs is not well understood, the influence of adsorbed proteins has been implicated. Recently it was reported ("Pseudomonas attachment to low-water and high-water and non-ionic, new and rabbit worn soft contact lenses", Brussel et al, Investigative Ophthalmology and Visual Science, 32, 657, 1991) that both new and worn SCLs can bind amounts of $p.$ $aeruginosa$ that could potentially produce bacterial keratitis.

SCLs in the eye are readily coated with tear proteins, mucus and lipids (Tripathy et al., "Lens Spoilage in Contact Lenses", in The CLAO guide to basic and applied clinical practice", Dabecies O. H. Jr. (Ed), Grune and Stratton Inc., Orlando Fla., 1984). $P.$ $aeruginosa$ is the responsible microorganism in up to two thirds of the reported cases of extended wear SCL associated infectious keratitis. The extended wear contact lens induces corneal hypoxia, microtrauma and tear film destruction that weaken corneal defense.

It is therefore a principal object of the present invention to provide a catheter for use in urological surgery or for managing urinary incontinence which inhibits the build up of encrustation on the surface of the catheter.

Another object of the present invention is to provide a catheter for use in urological surgery or for managing urinary incontinence which causes a lower risk of infection than known catheters.

It is yet another object of the present invention to provide a coating for contact lenses, particularly of the extended wear type, which inhibits the adhesion of harmful bacteria on the lens surface.

SUMMARY OF THE INVENTION

There is a clear need to develop biopolymeric interfacial surfaces which minimize bacterial adhesion. The present invention describes such a surface with two specific examples: one a urinary catheter and another a contact lens. Urinary catheters of the present invention are made of materials that a) prevent the adherence of bacteria, b) inhibit urease, and c) prevent calcium and magnesium phosphate deposits on the material. Such urinary catheters are especially useful when intended for use for extended periods. The invention includes the surface modification of high surface area carbon by means of a reactive hydrophilic polymer which forms a composite when painted on a braided nylon. The carbon modified polymer paint can be coated on all plastic materials including latex. The coated catheter remains flexible and hydrophilic and allows equilibration of ions and offers a reactive surface. This invention has been extended to apply to contact lenses. Lenses coated with carbon-free formulations of the present invention show excellent resistance to $P.$ $aeruginosa$. Certain chemical modification schemes of the surface of the contact lens were also successful.

The present invention differs from the prior art in several ways: 1) it uses antibacterials that could covalently bind to the —NCO group of a prepolymer such that the antibacterial would become a part of a hydrophilic polyurethane backbone of the coating, 2) it uses an oxidized high area carbon which is extremely effective in binding $Ag^+$ ions and antibacterials such as polymyxin through its carboxylic groups. The COO— groups can also bind cationic ingredients such as aminopolycarboxylic acids and their derivatives capable of chelating $Ca^{2+}$ and $Mg^{2+}$ coupled with $Ag^+$ which is a urease inhibitor along with antibacterials such as fluoroquinolones, quinolones and other antibacterials make the coating of the present invention a triple defense system. 3) It uses cyanuric chloride (trichloro-s-triazine) as a coupling agent to react with hydroxyl groups on surfaces.

BRIEF DESCRIPTION OF THE DRAWINGS

FIG. 5 is a plot of bacterial adhesion data for $P.$ $Mirabalis$ for all samples including the silicone and Teflon controls.

FIG. 6 is a plot of bacterial adhesion data for $P.$ $Mirabalis$ for the samples from the present invention only.

FIG. 7 is a plot of bacterial adhesion data for $P.$ $Vulgaris$ for all samples including the silicone and Teflon controls.

FIG. 8 is a plot of bacterial adhesion data for $P.$ $Vulgaris$ for selected samples along with the controls.

FIG. 9 is a graph showing the effect of different treatments on the bacterial adhesion on IV catheter materials.

FIG. 10b is a cross sectional view of the lens shown in FIG. 10a.

FIG. 10d is also a cross sectional view of the contact lens of the type shown in FIG. 10a.

DETAILED DESCRIPTION OF THE PREFERRED EMBODIMENTS

Figure 1:
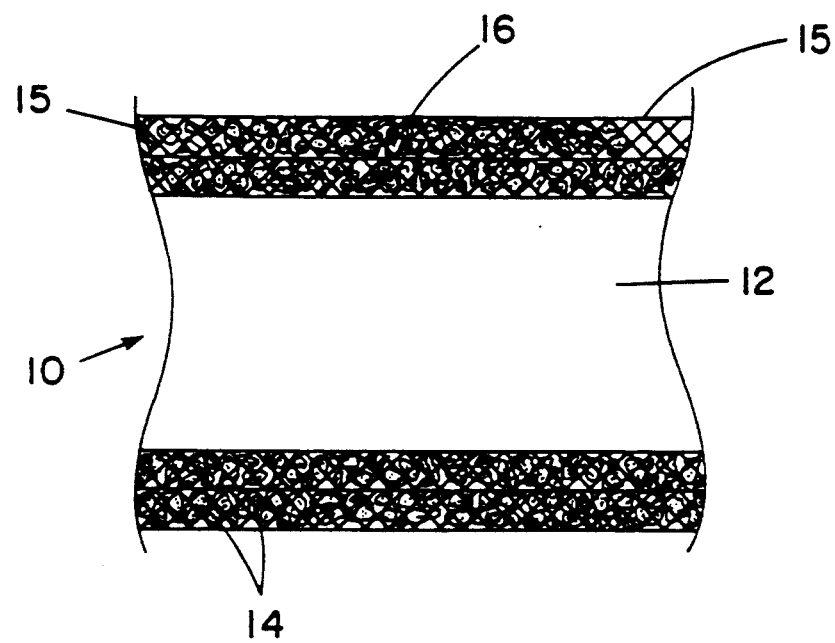
FIG. 1 is a sectional view of the coating configuration of the present invention.

The following is a detailed description of two embodiments of the present invention:

Urinary Catheter: The coating for catheters of the present invention that minimizes encrustation and/or infection, as encountered in known urinary catheters includes a coating having a hydrophilic polyurethane prepolymer, a high area filler which is preferably carbon, (but silica or alumina and other agents may be used which chelate calcium and magnesium in the body fluids that cause encrustation), anti-bacterial agents such as quinolones and urease inhibiting agents such as silver ions and EDTA.

Aminopolycarboxylic acids such as ethylene diamine tetraacetic acid, and iminodiacetic acid are powerful chelating agents for Ca and Mg at pH's between 8-10. At pH=7, (the normal urine pH), ethylene diamine tetraacetic acid exists mostly in the form of $H_2 Y^{2-}$ ($Y^{4-}$ is the tetra ion) and small amounts of $Y^{4-}$, $H_3 Y^-$ and $H_4 Y$. At pH 10, the concentration of $Y^{4-}$ is 40% of the total concentration of the ethylene diamine tetraacetic acid. In a situation where $H_2 Y^{2-}$ is present on the biomaterial in reasonably high concentration, the increase in pH due to urease action will be somewhat controlled due to the release of the acidic protons and any further increase would result in the formation of $Y^{4-}$ which will engulf $Ca^{2+}$ and $Mg^{2+}$ at pH values between 8 and 10 and prevent the nucleation of hydroxyapatite and struvite on the catheter surface. When the pH of the urine becomes 7, the bound calcium and magnesium are released by ethylene diamine tetraacetic acid. It must also be noted that when the pH of the urine approaches 5 or below, ethylene diamine tetraacetic acid can act as powerful urease inhibitor and also possesses antibacterial properties by chelating $Ca^{2+}$ from the cell wall. Therefore the advantages of using ethylene diamine tetraacetic acid and related ligands at both high and slightly below neutral pH are highly beneficial in achieving the goals described above.

Among the antibacterial agents the quinolones are currently undergoing more innovation, and the interest far exceeds that in the cefalosporins and aminoglycosides. The quinolones are bactericidal and the minimum inhibitory concentration, in general, increases in presence of divalent cations due to their tendency to form complexes. The use of resorcinol or resorcinol monoacetate antiseptic agent has already been established for external uses. Incorporation of resorcinol monoacetate in collagen based biomaterials show dramatic evidence of bacterial inhibition even at a 2% W/W concentration. When this functionality is bonded to the catheter surface, one might expect to see long-term antibacterial effects.

In order to enrich the surface by the organic functionalities, a polymer was used. Extensive search of different commercially available polymers revealed the availability of a hydrophilic polyurethane prepolymer sold by W. R. Grace under the trade name Hypol®. Hypol 5000 (a pale yellow, high viscosity liquid) which is a MDI based prepolymer that contains 2.55 meq/g of free —NCO group and its various reactions with —OH and —COOH groups are shown below.

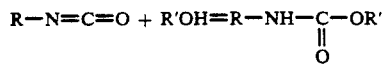

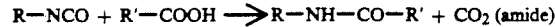

The highly reactive —NCO groups were reacted with ethylene diamine tetraacetic acid, iminodiacetic acid, resorcinol monoacetate, and quinolones. While several reaction sequences with different rate constants are possible during the coupling and curing processes, IR spectral data indicates the absence of —NCO groups and the presence of urethane, —COOH and —OH groups in the cured sample.

High area carbon can be used as an excellent support material for polymers such as Hypol. Diluted Hypol after chemical coupling with the appropriate compound blends very well with hydrophilic Cabot M-1300 carbon and forms a paint-like formulation. The surface area measurements of carbon loaded with Hypol tubings after complete cure showed an area of 3000 $cm^2/g$. The surface area of a silicone tube used as control in the experiments was only 270 $cm^2/g$. Thus the use of high area carbon in the formulation allows surface concentrations of the chelating and anti-bacterial agents to be at least one order of magnitude higher than what would be possible without the carbon. Hypol also proved to be an excellent binder for carbon and during all incubation studies of the various Hypol/Carbon catheter materials, microscopic carbon particles were not detected.

Once the modified Hypol (5-15% w/v in acetone) is diluted with dry acetone, addition of small amounts of Poly-Hema (4 ml of 12% w/v polyhydroxyethylmethacrylate in ethyl alcohol) and polyethyleneoxide, 300,000-9,000,000 molecular weight (2 ml of 5% w/v solution in methylene chloride) results in homogeneous dispersions. The resulting coatings showed greater lubricity and flexibility when exposed to water.

The high surface area of the carbon (>50 sq.m/g) coupled with its ability to provide reactive surface groups for the attachment of various ligands would facilitate a high surface concentration of the ligand moieties.

The urease concentration on the surface will be of micromole quantities. The aminopolycarboxylic ligands are capable of reversibly binding $Ca^{2+}$ or $Mg^{2+}$ depending upon the pH. Also the high surface concentrations of powerful urease inhibitors, such as $Ag^+$ along with antibacterials are expected to provide a powerful barrier against infecting bacteria and urease. The equilibration between the surface and the urine must be rapid due to the expansion of the hydrogel or ionomer coatings allowing diffusion of various species.

Nylon 6,6 fibers are used as support for the Hypol-carbon coatings; this support material allows the construction of tubings with different formulations and serves as a basis for proving the feasibility of this approach. The coated tubes can themselves be used as collapsible catheter material, although, several other designs are possible. An Ag-nylon material has also shown excellent adhesion to Hypol-carbon paint compared to plain nylon 6,6. The results also show better microbial protection when Ag-nylon is used in combination with ethylene diamine tetraacetic acid. The nylon/Hypol ® tubing were quite rigid, and would not collapse under normal usage.

The coating configuration is shown in FIG. 1 as a longitudinal cross section of a portion of the catheter tube 10. The cross-hatched portion 11 is the nylon weave which is braided onto a plastic core (not shown). This core is removed after the coating process to obtain the catheter tube 12. The granular material 14 shown in FIG. 1 in the nylon braid 15 represents the carbon black. The nylon braid 15 is completely covered with the Hypol/carbon paint 16. All the coatings were moisture cured overnight at room temperature and the coated tubes were stored at room temperature.

The term incorporation implies special methods of covalent attachment of the reagents on high surface area carbon followed by hydrogel encapsulation of carbon. Active carbon has been successfully encapsulated and has been used in the removal of toxins from blood. The hydrogel coatings reinforced with carbon and nylon fibers show superior mechanical strength compared to pure hydrogel coatings.

Contact Lens Application: Infective ulcerative keratitis is one of the most severe hazards of hydrogel extended wear soft contact lenses. Three new approaches are presented here to overcome this problem.

The first approach is based on the reactivity of trichloro-s-triazine (cyanuric chloride) toward —OH groups on the soft contact lens material surface. Cyanuric chloride (CC) as a coupling agent has been used in certain controlled delivery systems and has been proven to be safe (Petrak, K., 'Pharmaceutical Applications of Functionalized Polymers', in Reactive Polymers, vol. 10, page 231, 1989). Even though cyanuric chloride is toxic due to the active chlorine, once the chlorides are coupled to IDA or EDTA moieties, the resulting structure is inert and non-toxic. The resulting ether linkages are inert to hydrolysis. In the present invention, chemical modification procedures will initially prepare in situ IDA or DPTA-CC which will be further reacted with SCL. The CC-IDA or CC-DPTA aqueous solutions have no odor and can be easily handled. This treatment will result in the formation of a layer of covalently bound active functionalities. The coverage on the surface of the contact lens will be at monolayer levels.

Figure 10C:
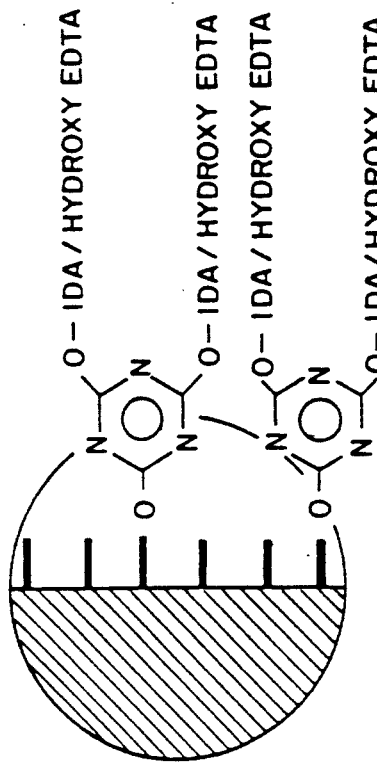
FIG. 10c is an expanded schematic of the covalent coupling of diaminopropanoltetra acetic acid to the lens surface through a bridge of cyanuric chloride.
Figure 10E:
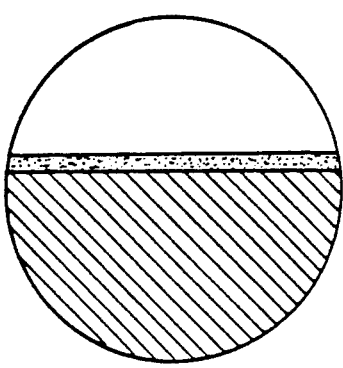
FIG. 10e shows an enlarged view of a thin coating of Hypol®/Polyox® coating as explained in Example 10.
Figure 10B:
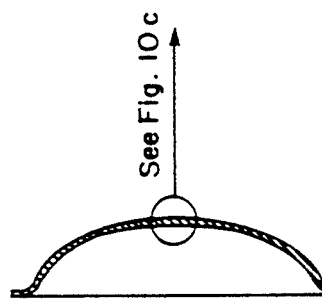
Figure 10D:
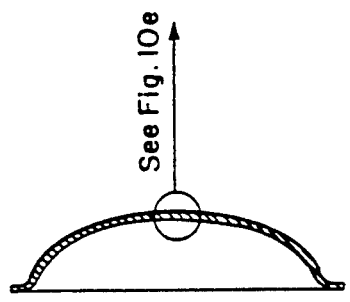
Figure 10A:
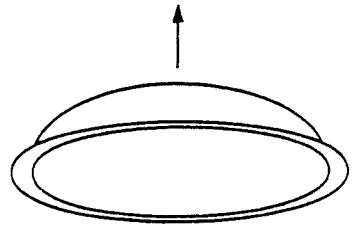
FIG. 10a is a perspective view of a contact lens.

A schematic illustration of the coating process is shown in FIG. 10a–10c. FIG. 10a shows a side view of the surface modified contact lens. FIG. 10b is a cross sectional view of the lens. FIG. 10c shows an enlarged view of the binding of the DPTA or IDA to the lens surface through cyanuric chloride bridge. Such treatments and covalent linking can also be achieved using cyanogen bromide or cyanogen chloride as the coupling agent.

Covalently bound chelating agents like DPTA could still bind $Ca^{2+}$ and disrupt the cell wall of the bacteria. The same chelating effect is expected of iminodiacetic acid which readily bonds to CC. These bactericidal agents, functioning by their cation complexing action upon the cell wall do not need to be incorporated into the bacterial cell to be effective as bactericides. As an added protection, a water soluble antibiotic such as polymyxin sulfate B (a large cation) can be bound to the $COO^-$ rich surface. (This antibiotic is presently used as a topical medication for contact lens related infections).

Polymyxins are one among the very few antibiotics which are known to inhibit *P. aeruginosa*. The group of polymyxin includes closely related circulins and colistins. These are closely related to cyclic lipopeptides. They are branched cyclo- octa, deca or undeca peptides that are monoacetylated in the aminoacyl side chains with branched chain fatty or β-hydroxy fatty acids. These antibiotics are characterized by a high percentage of $α, τ$-diaminobutyric acid, the presence of several aminoacids and a heptapeptide ring and by the fatty acid attachment to the N-terminal of the peptide side chain through an amide bond. The polymyxins are deca-peptides containing $C_8$ or $C_9$ fatty acids.

The second approach is based on the discovery that polymyxin sulfate B is capable of adsorbin on the polyhema surface of the contact lens. There is evidence in the literature on the irreversible adsorption of different drugs on the poly-HEMA surface. In the present invention, it was found that polymyxin B sulfate in contact with the surface of the Surevue lenses, was irreversibly bound. This discovery is further explained in Example 11, where it is shown that after treatment with polymyxin B sulfate, and several rinses of the lens, no bacterial adhesion is found.

Our invention that polymyxin B is extracted by polyhema contact lens and retained after several washings can be explained on the basis of solubilities of various lipophilic drugs in p. hema. Drugs such as chloramphenicol, pilocarpine, dexamethasone etc., were found to have a longer washout period when entrapped in intraocular lenses (T. P. Heyrman, M. L. McDermott, J. E. Ubels and H. F. Edelhauser, in Journal of Cataract Refractory Surgery., vol 15, page 169, 1989). Gentamicin soaked contact lenses made of 61.4% p. hema hydrogel were found to retain bactericidal concentrations of the antibiotic for three days of eye contact (M. Busin, M. Spitznes, Ophthalmology, vol 95, page 796, 1988). Ionic binding of cationic polymyxin by the anionic carboxyl groups is also possible.

In another approach, an optically clear, adherent coating can be obtained using Hypol ® in combination with small amounts of polyethylene oxide with or without antibacterials. A schematic illustration of such a coating is shown in FIG. 10d, with FIG. 10e showing an enlarged view of the coating on the lens surface. The cured coatings incorporate, by covalent bonding, the organic functionalities in the polyurethane backbone. The prepolymer polyurethane forms a clear, highly adherent, hydrophilic coating on the soft contact lenses.

EXAMPLE 1

10 g of Hypol 5000 ( a hydrophilic polyurethane prepolymer, MDI based, 2.5 meq. NCO per gram, W. R. Grace) was weighed into a polypropylene cup and 5 mmoles each of ethylene diamine tetraacetic acid, iminodiacetic acid, resorcinol monoacetate, and nitroxolin were added, and stirred well. To this mixture was added dry methylene chloride (70 ml), a few drops of a surfactant, Pluronic L-101. The mixture was homogenized with a homogenizer or sonicator and used for coating after the addition of dry carbon (Carbon black, M-1300, Cabot Co., 7 g). Desired consistency is obtained by the addition of more solvent. All formulations hardened within 2–4 hrs. The coatings consisted of a) Hypol-ethylene diamine tetraacetic acid/C b) Hypol-resorcinol monoacetate/C c) Hypol—Nitroxolin/C and d) Hypol-iminodiacetic acid/C. Coatings were done using a dip coating machine on pretreated nylon 6,6 fibers and silver nylon (Charles Reiner Co) fibers. A smooth uniform tube of approximately 2.5 mm diameter is obtained, which is used in the experiments described in Examples 2–8.

EXAMPLE 2

Magnesium Binding Capacity of the Coated Surfaces: Typically 6" long coated tubes were incubated in an ammonium chloride/ammonium hydroxide buffer (pH=10) containing 0.04M of Mg. After four hours of incubation, the samples were rinsed with ammoniacal water and the solution was titrated against standardized ethylene diamine tetraacetic acid. The ethylene diamine tetraacetic acid immobilized surface showed a magnesium uptake of 0.31 remoles in excess of what was absorbed by a sample not containing immobilized ethylene diamine tetraacetic acid.

EXAMPLE 3

3" samples of the materials were soaked in 30 ml of synthetic urine (pH=5.8) for 2.5 hours, after which 25 units of urease solution was added and maintained at 37° C. overnight.

For all the urease inhibition experiments, synthetic urine was used. Synthetic urine was prepared as described in Griffith, D. P., Musher, D. M., and Itin, C., "Urease - The Primary Cause of Infection Induced Urinary Stones", Investigative Urology, 13, 346 (1974) with the following composition (Table I).

TABLE I

COMPOSITION OF SYNTHETIC URINE
(Griffith et al., 1976)

| Chemical | Concentration (g/L) |
| --- | --- |
| $CaCl_2.2H_2O$ | 0.65 |
| $MgCl_2.6H_2O$ | 0.65 |
| NaCl | 4.60 |
| $Na_2C_2O_4$ | 0.02 |
| $KH_2PO_4$ | 2.80 |
| KCl | 1.60 |
| $NH_4Cl$ | 1.00 |
| Urea | 25.00 |
| Creatinine hemisulfate | 1.10 |
| Uric acid | 0.25 |
| Bovine Serum Albumin | 0.50 |
| pH adjusted to | 5.80 |

TABLE II

RESULTS OF OVERNIGHT INCUBATION OF CATHETER TUBE SAMPLES (3") IN SYNTHETIC URINE CONTAINING UREASE.

| Sample # | Description | Observation |
| --- | --- | --- |
| 1A | nylon 6,6/C/Hypol/ | dense precipitate |
| 11 | nylon 6,6/C/Hypol-EDTA | moderate precipitate |
| 3A | nylon 6,6/C/Hypol-IDA | moderate precipitate |
| 6 | Ag-nylon/C/Hypol | dense precipitate |
| 3 | Ag-nylon/C/Hypol-IDA | very small amount of ppt. pH = 7.06 |
| 2 | Ag-nylon/C/Hypol-EDTA | Clear solution pH 6.88 |

The polymer bound chelating agents (ethylene diamine tetraacetic acid, iminodiacetic acid) show almost no precipitation of Ca and Mg.

EXAMPLE 4

3" samples of the materials were soaked in 30 mL of synthetic urine for 2.5 hours and varying amounts of urease solution was added and incubated at 37° C. for 48 hours.

TABLE III

RESULTS OF INCREMENTAL ADDITIONS OF UREASE TO SYNTHETIC URINE (37° C.) CONTAINING SAMPLES (3") AS DESCRIBED

| Sample # pH | Description | Units of urease | Final |
| --- | --- | --- | --- |
| 2 | Ag-nylon/C/Hypol-EDTA | 25 | 6.88 |
| 3 | Ag-nylon/C/Hypol-IDA | 25 | 7.06 |
| 1A | nylon/C/Hypol | 25 | 8.64 |
| 6A | Ag-nylon/Hypol | 25 | 8.46 |
| 6 | Ag-nylon/C/Hypol | 25 | 7.22 |
| 2 | Ag-nylon/C/Hypol-EDTA | 25 | 7.06 |
| 6B | Ag-nylon | 25 | 8.74 |
| Silicone | control | 55* | 9.13 |
| 1A | nylon/C/Hypol | 55* | 9.10 |
| 6 | Ag-nylon/C/Hypol | 55* | 8.47 |
| 2 | Ag-nylon/C/Hypol-EDTA | 55* | 7.16 |
| 6A | Ag-nylon/Hypol | 145* | 8.46 |
| 6 | Ag-nylon/C/Hypol | 145* | 8.62 |
| 2 | Ag-nylon/C/Hypol-EDTA | 145* | 7.39 |
| 6B | Ag-nylon | 145* | 8.74 |

*in increments of 30 units per day.

The data in Table III shows that the polymer bound chelating agents (ethylene diamine tetraacetic acid, IDA) show minimal rise in pH, and the solutions show little precipitation in these cases. Sample #2, 3 and 6 (for 25 units of urease only) samples clearly stand out with pHs in the range 6.8–7.5; sample #2 is particularly good, since the solution containing this sample remained clear, even when the pH rose to 7.8.

EXAMPLE 5

This is a slight variation of Example 4. 40 units of urease was added to 20 mL of synthetic urine (pH=5.8) and incubated at 37° C. for 1 hour. The solution became turbid; two portions of this turbid solution were used to incubate 3" samples of 1A (Hypol/C/nylon 6,6) and 11 (Hypol-ethylene diamine tetraacetic acid/C/nylon 6,6) overnight. Sample containing 1A shows a pH of 9.1 with dense precipitate. Sample containing 11 showed an almost clear solution with a pH of 8.0.

The results shown above prove the chelating ability of ethylene diamine tetraacetic acid is retained when it is bound to a polymer backbone as evidenced by its ability to dissolve calcium precipitate formed at pH's above 8. The dissolution process is slow (6–8 h). This observation is supported by the data in the literature (Burns, J., and J. G. Gargill, "Kinetics of Calcium Oxalate Calculi with Calcium Chelating Irrigating Solutions", J. of Urology, 39, 530 (1987)) on the kinetics of dissolution of calcium oxalate by ethylene diamine tetraacetic acid: it is reported that the rate of dissolution is slow even when sodium ethylene diamine tetraacetic acid is in solution. However, for a surface containing immobilized ethylene diamine tetraacetic acid rapid nucleation of hydroxyapatite will be prevented at least near the immediate vicinity of the surface, due to presence of the following equilibrium:

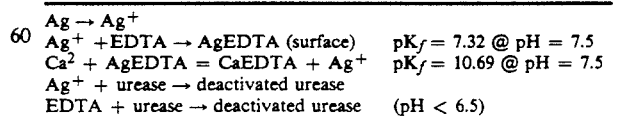

| | |
| --- | --- |
| $Ag \rightarrow Ag^+$ | |
| $Ag^+ + EDTA \rightarrow AgEDTA$ (surface) | $pK_f = 7.32$ @ pH = 7.5 |
| $Ca^2 + AgEDTA = CaEDTA + Ag^+$ | $pK_f = 10.69$ @ pH = 7.5 |
| $Ag^+ + urease \rightarrow$ deactivated urease | |
| EDTA + urease → deactivated urease | (pH < 6.5) |

EXAMPLE 6

Figure 2:
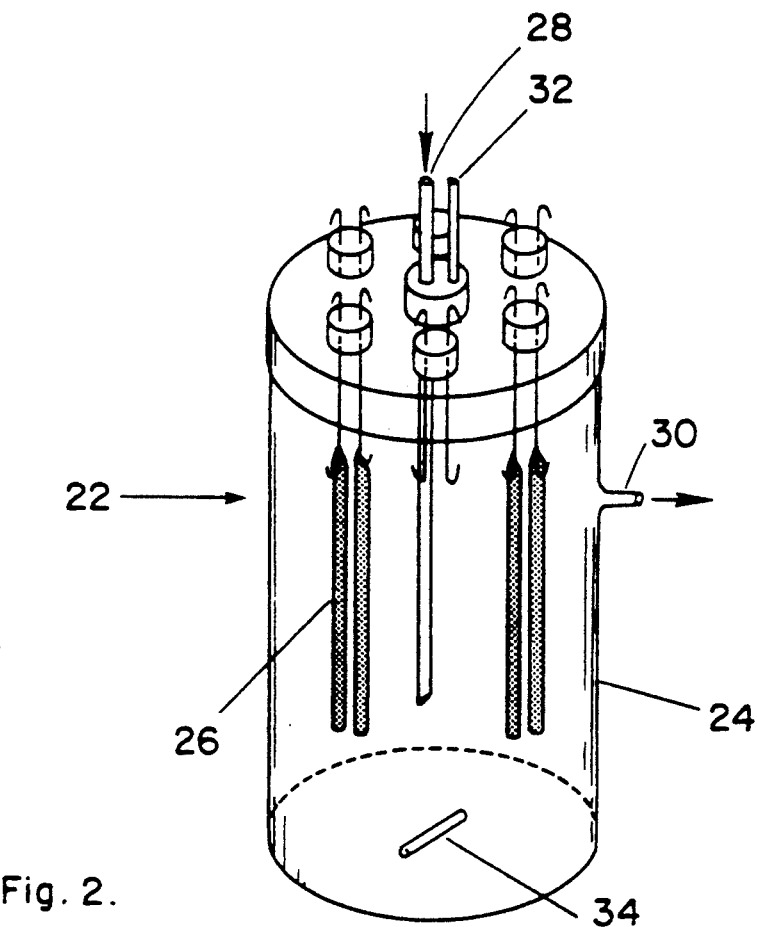
FIG. 2 is a perspective view of apparatus used to study the encrustation of urinary catheter samples coated in accordance with the present invention.

The apparatus 22 used is shown in FIG. 2. Artificial urine was added into an experimental vessel 24 (where the catheter tubes 26 were suspended). The vessel should have an inlet 28 and an overflow outlet 30. A vent 32 is also provided. The experimental vessel 24 was gently stirred with magnetic stirrer 34 while incubating at 37° C. The catheter samples were suspended in artificial urine for eighteen days. 200 units of urease were added per day and the urine changed every day. The addition of urease was carried out in increments of 50 units/2 hr. using a plastic syringe. (The urease solution was prepared by dissolving urease tablets in 10 mL sodium phosphate buffer, pH=7.1). In all tests, there were no signs of encrustation for about 1 week after which light white deposits started appearing on the surface. Perhaps due to the stirring no crystalline material was seen. Instead amorphous, loose deposits were seen. At the end of eighteen days, the sample tubes were carefully rinsed with deionized water and carefully dried after putting the individual pieces in preweighed clean vial. This ensured the loss of powdery deposits after drying. The dried samples were dessicated before weighing. After the weight of the encrusted tube was obtained, the tube was immersed in dilute HCl for about 2 minutes, dried with paper towel and then in an oven at about 50° C. overnight. An activated molecular sieve dessicant was kept in the oven to ensure the removal of moisture.

Samples tested using the urease encrustation model per the procedure of Cox, A. J., Hakins, D. N. L., and Sutton, T. M., "Comparison of in vitro Encrustation on Silicone and Hydrogel Coated Latex Catheters", Br. J. of Urology, 61, 156 (1988) were chiefly urease inhibiting and chelating surfaces. During this experiment the initial pH rise was slow (2 days, 5.8-6.2), and over a period of 14 days rose to 8.3. The initial resistance to pH rise may be attributed to silver ion released from the Ag-nylon in presence of ethylene diamine tetraacetic acid. The results of this experiment are plotted in FIG. 3 as weight gained per unit area (mg/cm$^2$).

Figure 3:
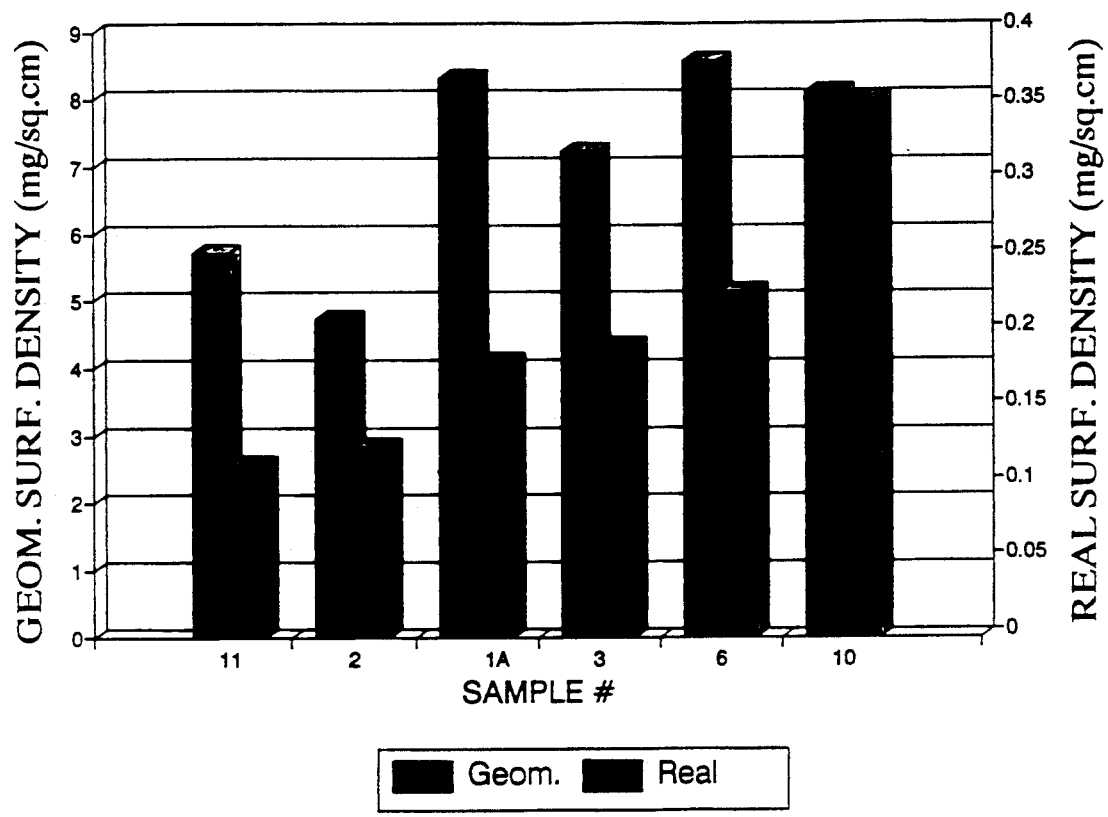
FIG. 3 is a graph showing encrustation weight per unit area, for the Urease Encrustation Model in which the Y-axis on the left shows weight rationalized on the basis of geometric area and Y-axis on the right shows the data for real surface area.

The urease addition test model resulted in variable encrustation of all samples in FIG. 3. The surface density of the encrustation were calculated based on the geometric area exposed to the synthetic urine. The results clearly show that the ethylene diamine tetraacetic acid modified surface has low encrustation. The results are even more dramatic if the real surface areas are used for calculating the surface density; the best samples constructed in accordance with the present invention show almost an order of magnitude less encrustation than silicone tubing. Visual inspection of the samples showed chunky white deposit on the silicone tube, whereas only a white powdery layer on the samples constructed in accordance with the present invention. It appears that the loose powdery deposits on the materials constructed in accordance with the present invention could easily be washed by the urine flow, whereas the highly adherent deposits on silicone may not come off easily. It appears that the large surface area of the samples of the present invention modifies the nucleation process resulting in a powdery layer.

The extent of encrustation is clearly related to the presence of antibacterials, chelating agents and urease inhibitors. An optimum combination of the three could prove better than just one defense mechanism. The extent of encrustation should also be dependent on the surface concentrations of the three classes of compounds. It must be emphasized that the test catheter tubes contained only 0.5 mmoles/g of Hypol in the coating; only two coatings (4 mil total) of this material was loaded on the nylon support.

EXAMPLE 7

For these experiments, a dynamic perfusion model was used. The apparatus 22 used in this example is shown in FIG. 2. Artificial urine was allowed to flow into an experimental vessel 24 (where the catheter tubes 26 were suspended) at a controlled rate (1.2 L/day). The vessel should have an inlet 28 and an overflow outlet 30. A vent 32 is also provided. Proteus mirabalis was cultured in Trypticase soy broth/urea agar medium by using a cultiloop (BBL labs). The experimental setup was inoculated with enough bacterial broth to give a turbidity of McFarlane #1 and was checked for bacterial count of $1\times10^6$/mL. The experimental vessel 24 was gently stirred with magnetic stirrer 34 while incubating at 37° C. Bacterial counts were checked everyday in the outflowing liquid.

Figure 4:
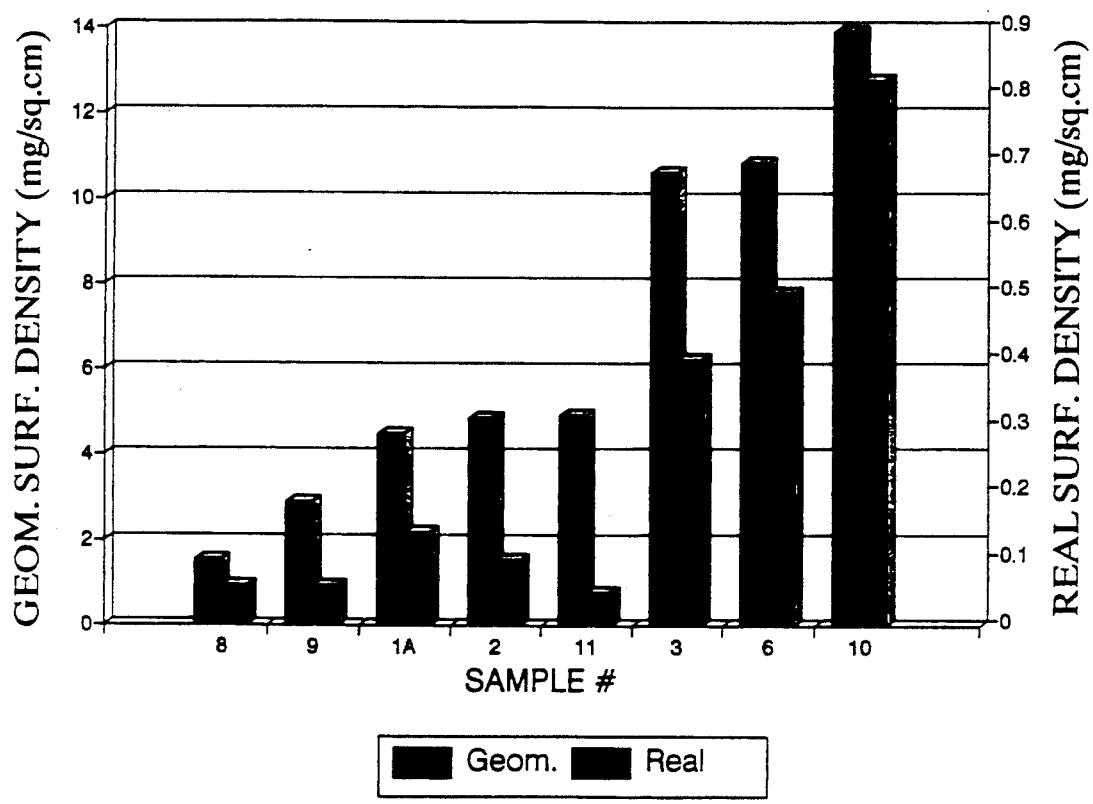
FIG. 4 is a graph showing encrustation weight per unit area, for the Bacterial Encrustation Model in which the Y-axis on the left shows weight rationalized on the basis of geometric area and Y-axis on the right shows the data for real surface area.

The bacterial encrustation model results shown in FIG. 4 indicate that antibacterial agents lower the encrustation more efficiently than chelating agents and urease inhibitors.

The bacterial encrustation along with the urease inhibition study indicate relatively low amounts of encrustation for surfaces modified by ethylene diamine tetraacetic acid. It appears that Hypol bound ethylene diamine tetraacetic acid still maintains its chelating ability. In addition, the large surface area of the carbon loaded polymer coating appears to allow physical deposition of hydroxyapatite rapidly as the pH rises resulting in a powdery precipitate. The solubilizing action of ethylene diamine tetraacetic acid helps loosen the deposit. It appears that the antibacterial properties of ethylene diamine tetraacetic acid coupled with its ability to chelate $Ca^{2+}$ could be advantageously used for catheter coatings. The chief advantage of ethylene diamine tetraacetic acid modified surface is that at pH values below 8, protons compete very efficiently with $Ca^{2+}$ ions, thus regenerating the surface enriched with uncomplexed ethylene diamine tetraacetic acid. At pH values below 6 ethylene diamine tetraacetic acid complexes nickel centers from urease and thus becomes an urease inhibitor. As the pH of the urine rises due to urease action complexation with $Ca^{2+}$ and $Mg^{2+}$ occurs with the release of protons. Therefore in the final form the catheters could revive their surface if the patient's urine becomes slightly acidic. Since the inner surface of the catheter is more prone to encrustation, it is possible to incorporate ethylene diamine tetraacetic acid on the inner surface essentially by the same methods.

The outer surface of the catheter could contain simply antibacterials or lower surface concentration of ethylene diamine tetraacetic acid. These tubes can even be used as inner inserts for regular Foley catheters with appropriate redesign.

EXAMPLE 8

Cultures and cultural conditions: Two bacterial strains, Proteus mirabilis and Proteus vulgaris, were used in these experiments. Proteus mirabilis was grown anaerobically in Trypticase Soy broth (Difco), incubated in Brewer Anaerobic Jars with 80% $N_2$, 10% $CO_2$, and 10% $H_2$. Proteus Vulgaris was grown in Trypticase Soy broth aerobically. All cultures were incubated at 35° C. Bacteria were labeled in T. Soy broth supplemented with 5 $\mu$Ci/ml$^3$H-Thymidine, harvested by centrifugation, and washed twice with synthetic urine (SU), pH 5.8. For the adhesion assay, the bacteria were re-suspended in SU at a final concentration of $5 \times 10^6$ bacteria/ml.

Sample Preparation: Twelve catheter samples were used in these experiments including a silicone control. The samples were sectioned using sheers into 2.5 mm ($\pm 0.5$ mm) pieces and weighed. For assays utilizing single sections of catheters, one piece of catheter/well was placed in 96 well microtiter plates. For larger volume assays, three sections from each sample were placed in 1.5 ml centrifuge tube.

Assay: After sectioning, the samples were washed with 150 μl or 450 μl SU (based on volume of assay). The catheters were incubated with either 120 μl or 1.0 ml of the appropriate bacteria at $5 \times 10^8$/ml SU, for 1 hour, rotated at 6 rpm, at 35° C. Non-adherent bacteria were removed by washing 3 times with either 150 μl or 450 μl SU. The samples were transferred to scintillation vials and cpm were determined by means of a Packard scintillator.

The data consist of bacterial counts ($\times 10^5$) on the surfaces of four different samples from each of twelve catheter materials using two bacterial types: *P. Mirabalis* and *P. Vulgaris*. The counts for the former are an order of magnitude higher than for the latter and they will be analyzed separately. However, the sample coding is the same for both data sets and is presented in Table IV. Two of the catheter materials (i.e., silicone and Teflon coated latex) are in current clinical use and serve as controls for comparison with the other experimental materials. The data was analyzed using the Systat statistics software package, version 4.0.

TABLE IV

| CATHETER MATERIAL CODES | |
|---|---|
| Sample # | Description |
| 1 | nylon/C/Hypol/Nafion |
| 1A | nylon/C/Hypol |
| 2 | Ag-nylon/C/Hypol-EDTA |
| 3 | Ag-nylon/C/Hypol-IDA |
| 3A | nylon 6,6/C/Hypol-IDA |
| 4 | nylon 6,6/C/Hypol-EDTA/Nafion |
| 5 | nylon/C/Hypol-RMA/Nafion |
| 6 | Ag-nylon/C/Hypol |
| 6A | Ag-nylon/Hypol |
| 6B | Ag-nylon |
| 7 | nylon/C/Hypol-Bufexemac |
| 8 | nylon/C/Hypol-Nitroxolin |
| 9 | nylon/C/Hypol-RMA |
| 10 | Silicone |
| 11 | nylon 6,6/C/Hypol-EDTA |
| 12 | Latex/Teflon |

The bacterial adhesion data for *P. Mirabalis* is plotted in FIG. 5. (An outlier, with a Studentized Residual = 10.08 in sample 1, was removed and not included in FIG. 5). As Indicated by ANOVA analysis, ($P=0$), there are significant differences in adhesion between the various samples. Clearly, the two "controls", code = 10 (silicone) and code = 12 (latex/Teflon), appear to promote greater *P. Mirabalis* adhesion than any of the materials coated in accordance with the present invention. This conclusion is confirmed by the results of a t-test in which the two controls combined are significantly different ($P=0$) from all the materials coated in accordance with the present invention combined.

The data for the materials coated in accordance with the present invention alone is plotted in FIG. 6 with a reduced Y axis scale to highlight differences between these materials. Several advantages are apparent. First, the highest adhesion results were obtained with sample code = 1 and sample code = 7. However, both are still better than the combined silicone and Teflon controls (t-test, $p < 0.001$). Second, where a direct comparison can be made, i.e., sample 2 vs. sample 3, the two aminopolycarboxylic acids are clearly similar in bacterial adherence. Third, the quinoline derivative nitroxolin (sample 8) yielded the lowest adhesion results.

The data summary for adhesion to the various samples in Table IV to *P. Vulgaris* is presented in FIG. 7. In general, the adhesion is much lower than with *P. Mirabalis*, however, there are significant differences among the samples as shown by ANOVA analysis ($P=0$). Sample 1 shows the most bacterial adherence and actually appears greater than the silicone and Teflon controls; however, a t-test does not quite reach significance ($P=0.08$). Clearly, samples 2,3,7,9 are within the range of the silicone and Teflon controls and cannot be said to have reduced *P. Vulgaris* adhesion. Samples 4,5,6, and 8 performed the best of the materials coated in accordance with the present invention, and showed a highly significant difference, compared to the combined controls ($P=0.001$). The only pattern that is repeated here compared to the *P. Mirabalis* results is that sample 8, the quinoline derivative nitroxolin, again showed the lowest adhesion, and the Ag-nylon/C/Hypol (sample 6) also performed well with both organisms.

Selected samples were rerun using larger sample pieces in order to increase the bacterial count and achieve greater precision. The results are plotted in FIG. 8. This set included nylon/C/Hypol control. ANOVA analysis shows a significant difference among these samples as might be expected ($p < 0.02$). The silicone and Teflon/latex controls appear to cause much greater adherence than any of the samples coated in accordance with the present invention. The difference between the combined controls and the combined samples coated in accordance with the present invention is highly significant ($p < 0.01$). When Ag and ethylene diamine tetraacetic acid are present together, the bacterial adhesion is significantly less ($p < 0.03$) than the control with only nylon/C/Hypol. However, Ag alone or ethylene diamine tetraacetic acid alone does not show significant difference in adhesion compared to the samples not containing these ($p > 0.05$). The second set of data generally confirm the conclusions from the first study.

The above results show that the silver nylon or silver nylon-Hypol combinations do not inhibit urease effectively under the conditions these experiments were carried out. One explanation could be the low concentration of $Ag^+$ further reduced by the formation of AgCl when the samples are incubated in synthetic urine. In the Hypol matrix, it appears that the $Ag^+$ is immobilized in a highly insoluble form. Whereas the Ag nylon/ethylene diamine tetraacetic acid inhibits urease, under the same conditions the silver nylon/Hypol alone without the ethylene diamine tetraacetic acid, does not. The antibacterial properties of silver nylon suture and wound dressing materials is based upon the slow release of enough silver ions (which are toxic to bacteria). Experimental evidences based on extractions of $Ag^+$ from a given quantity of silver nylon at 37° C. prove that the Ag nylon may function as a reservoir of $Ag^+$ ions (Chu et al., 1988; Tsai et al., 1987).

EXAMPLE 9

This example illustrates the use of the invention described above as a paint for various catheter surfaces or devices. Polyurethane tubes (e.g., Tecoflex EG80A) were coated with Hypol/carbon mixtures containing silver acetate, resorcinol monoacetate, and Norfloxacin. p. aeruginosa was used as bacterial strain. The bacteria were labeled with $^3$H-thymidine. The catheter samples were incubated in growth medium containing the labeled bacteria for 48 hours. At the end of the appropriate incubation period, the samples were washed and assayed using a scintillation counter. The results of bacterial counts for the four samples are compared to the control (polyurethane tube without any coating) in FIG. 9. From the results shown in FIG. 9, it is clear that all the treatments are better than the control.

EXAMPLE 10

Surface Treatment of Lenses: Surevue ® contact lenses which are manufactured by Vistakon ™ were used in these experiments. In one set of experiments, covalent coupling of DPTA was achieved using cyanuric chloride as coupling agent. Acetone rinsed lenses were exposed to a solution (4°–5° C.) containing cyanuric chloride dissolved in dry acetone (1–2% w/v). In other embodiments, cyanogen bromide may be used instead of cyanuric chloride as the coupling agent. After five minutes, the lenses were exposed to a clear 2–5% w/v solution of diaminopropanol tetracetic acid in 0.05M sodium hydroxide at about pH 7–8. In these experiments, other aminopolycarboxylic acids such as iminodiacetic acid can also be used. After stirring and soaking for fifteen minutes, the lenses were rinsed with distilled water several times. The lenses were then soaked in a solution containing polymyxin sulfate 5 mg/milliliters, for fifteen minutes. The lenses were then rinsed several times with distilled water and stored in commercial lens storage solutions. In a separate set, polymer modifications of a hydrophilic polyurethane prepolymer (Hypol ®) were accomplished using hyaluronic acid, resorcinol monoacetate, Nafion ® (a cationic resin with sulfonate groups), and Polyox ®. The lenses were rinsed in acetone three times and then dipped in the following solutions and allowed to dry:
Hypol (5% w/v solution in acetone) alone
100 mL of Hypol 5% in acetone +2–5 gram of pure resorcinol monoacetate
100 mL of Hypol 5% in acetone +2–5 g of Nafion 5% W/V in alcohol
100 mL of Hypol 5% in acetone +2–5 g of Polyox 5% W/V in methylene chloride
100 mL of Hypol 5% in acetone +1–2 g of Hyaluronic acid in water.

Thin uniform coatings were obtained with some practice. The coated lenses and appropriate controls were then immersed in a buffered saline solution, coded (to ensure a blind test), and stored for further tests.

Bacterial Adhesion Test Protocol: P. aeruginosa 6294 (from a human corneal ulcer) stored in tryptic soy broth and 10% glycerol at −70° C. was used as the bacterial strain. Approximately 100 ml from a 1 ml aliquot of p. aeruginosa frozen suspension was thawed and grown overnight at 37° C. in a tryptic soy agar (TSA) plate. Few colonies from the TSA plate were suspended in sterile phosphate buffered saline solution to a concentration adjusted spectrophotometrically to about $10^8$ cfu/ml (OD=0.1,=590 nm, Beckman DU-70 Spectrophotometer).

Each contact lens was divided aseptically (laminar flow hood) in half with a sterile razor blade in order to perform duplicate experiments. The divided half lenses were incubated statically in 1 ml bacterial suspension for 1 hour at room temperature. After incubation, the lenses were profusely rinsed in six aliquots of PBS to remove all firmly attached bacteria. The lenses were then ground with a glass rod and suspended in 10 ml of PBS. The suspension was diluted in 1:10 serial dilutions and cultured on TSA plates. The plates were incubated for 36 hours at 37° C. Colony growth was counted and the number of bacteria per half lens was calculated and expressed as colony forming units (cfu) per half a contact lens. For the purpose of normalization of results, the bacterial count observed with each control contact lens (uncoated sample) was taken to represent 100% adherence. The bacterial counts for all the coated samples were then normalized with respect to the control, and the % adherence in each case calculated.

Since the bacterial counts were done in two separate batches, one control for each batch was included to account for batch to batch variations in experimental methodology. After the bacterial adhesion results were obtained, the storage solutions of samples with minimum and maximum adherence along with adequate controls were assayed for their antimicrobial activity. In the case of assays involving storage solutions, an additional control in the form of the PBS buffer solution used in these experiments was included to obtain an idea about the bacterial growth in the medium without the influence of the contact lenses.

Test Results: The duplicate set of results of bacterial adhesion expressed as average cfu and % adherence are shown in Table V. The antimicrobial activity of the contact lens storage solutions is shown in Table VI.

TABLE V

| | BACTERIAL ADHESION RESULTS OF SURFACE TREATED CONTACT LENSES | | | |
|---|---|---|---|---|
| | EXPERIMENT I | | EXPERIMENT II | |
| TREATMENT | AVERAGE CFU/½ LENS ($\times 10^4$) | % ADHER. | AVERAGE CFU/½ LENS ($\times 10^4$) | % ADHER. |
| Control | 20 | 100 | 9.5 | 100 |
| CC-hyaluronic acid | 19 | 90 | 11.1 | 118 |
| Hypol-RMA | 23.8 | 120 | 2.1 | 2.22 |
| CC-PEO | 79 | 400 | 62 | 653 |
| Control | 25 | 100 | 9.7 | 100 |
| Hypol | 20 | 20 | 3.8 | 39 |
| Hypol-hyaluronic acid | 11.2 | 44 | 11.6 | 120 |
| Hypol-Nafion | 15 | 60 | 4 | 41 |
| CC-hydroxy EDTA-Polymyxin | 0 | 0 | 0 | 0 (cfu $\times 10^2$) |
| Hypol-PEO | 1.3 | 5 | 2.6 | 27 |

TABLE VI

ANTIMICROBIAL ACTIVITY OF THE CONTACT LENS STORAGE SOLUTIONS

| LENS STORAGE SOLUTION | CFU/mL ($\times 10^5$) 24 h incubation |
|---|---|
| control PBS | 3.3 |
| control 0 | 4.3 |
| control 1 | 2.9 |
| CC-hydroxy EDTA-Polymyxin | 3.5 |
| Hypol-PEO | 3.0 |
| Hypol-PEO | 3.6 |
| CC-PEO | 4.0 |

PBS = phosphate buffered saline;
CC = cyanuric chloride;
PEO = polyethylene oxide
EDTA = ethylene diamine tetraacetic acid,
RMA = resorcinol monoacetate It is evident from the above data that the polymyxin treated surface shows almost no adherence and the Hypol & Hypol-polyethylene oxide modified surfaces show greatly reduced adherence compared to the controls.

EXAMPLE 11

Three Surevue lenses were first rinsed in distilled water, followed by dipping in polymyxin sulfate solution (0.1 g/50 ml distilled water). After 5 minutes, the lenses were rinsed and soaked in distilled water in four different beakers and stored in the contact lens storage solution. When these samples were tested for bacterial adhesion using the same procedure as described in Example 10, we obtained the following results:

TABLE VII

BACTERIAL ADHESION RESULTS OF polymyxin TREATED CONTACT LENSES

| | EXPERIMENT I | | EXPERIMENT II | |
|---|---|---|---|---|
| TREAT-MENT | AVERAGE CFU/½ LENS ($\times 10^4$) | % ADHER. | AVERAGE CFU/½ LENS ($\times 10^4$) | % ADHER. |
| Control | 235 | 100 | 103 | 100 |
| polymyxin dipped (Example 11) | 2.28 | 1 | 0.17 | 0.2 |
| polymyxin coupled (Example 12) | 122 | 52 | 62 | 60 |

Table VII clearly shows the superiority of polymyxin dipped lenses. This is a simple process that results in the ionic bonding of the antibacterial on the contact lens surface. The lens storage solution from this example showed some bactericidal activity ($11.7 \times 10^4$ cfu/ml vs. $1.05 \times 10^4$ cfu/ml for the control) indicating an equilibrium between the adsorbed polymyxin and the solution.

EXAMPLE 12

The distilled water rinsed contact lenses were soaked in 1% cyanuric chloride in acetone, followed by exposure to a DPTA solution (3.66 grams of DPTA+2 grams of sodium hydroxide+100 ml of distilled water), followed by exposure to polymyxin B sulfate solution (0.1 g/50 ml water). The bacterial adhesion results from these lenses are shown in Table VII. The lenses show 50-60% adherence compared to the control. The incomplete bacterial inhibition in this example is attributed to the partial coverage of the lens by the immobilized polymyxin. Such imcomplete coverage can be remedied by careful control of pH. However, the important observation in this experiment is the solution activity of these lenses. The lens storage solutions did not show any bactericidal activity (Control solution: $1.05 \times 10^8$ cfu/ml vs solution from this example: $0.66 \times 10^8$ cfu/ml). The lack of bactericidal activity in the storage solution shows that the polymyxin is strongly bound to the surface.

While the foregoing invention has been described with reference to its preferred embodiments, various alterations and modifications will occur to those skilled in art. All such alterations and modifications are intended to fall within the scope of the appended claims.

What is claimed is:

1. A coating for polymeric products used in medical applications, said coating comprising:
   a reaction product formed by a covalent linkage of a hydrophilic polyurethane pre-polymer and aminopolycarboxylic acid.

2. The coating of claim 1 wherein said aminopolycarboxylic acid is selected from the group of ethylene diamine tetraacetic acid, diaminopropanol tetracetic acid and iminodiacetic acid.

3. The coating of claim 1 further comprising a high urea carbon compounded with said coating to provide a larger surface area of contact.

4. The coating of claim 1 further comprising a urease inhibitor.

5. The coating of claim 1 further comprising an antibacterial agent.

6. The coating of claim 5 wherein said antibacterial agent is from the quinolone family.

7. The coating of claim 5 wherein said antibacterial agent is a phenolic compound.

8. A coating for polymeric products used in medical application, said coating comprising:
   aminopolycarboxylic acid;
   a coupling agent for directly linking said aminopolycarboxylic acid to at least one surface of the said polymeric product.

9. The coating of claim 8 further comprising a high area carbon compounded with said coating to provide a larger surface area of contact.

10. The coating of claim 8 wherein said coupling agent is cyanuric chloride.

11. The coating of claim 8 wherein said coupling agent is cyanogen bromide.

12. The coating of claim 8 wherein said aminopolycarboxylic acid is selected from the group of diaminopropanol tetracetic acid and iminodiacetic acid.

13. The coating of claim 8 further comprising a urease inhibitor coupled with said aminopolycarboxylic acid.

14. The coating of claim 8 further comprising an antibacterial coupled with said aminopolycarboxylic acid.

15. A medical device which is resistant to the formation of encrustation or bacteria for use in medical applications, said device comprising:
   a base material formed in a desired shape;
   a coating covering at least one surface of said base material, said coating including
      a reaction product resulting from a covalent linkage of said hydrophilic polyurethane pre-polymer with a aminopolycarboxylic acid.

16. The device of claim 15 wherein said coating further comprises a high area carbon compounded with said coating to provide a large surface area of contact.

17. The device of claim 15 wherein said device is a urinary catheter.

18. The device of claim 15 wherein said base material is constructed from silver-nylon fibers.

19. The device of claim 15 wherein said device is a Foley catheter.

20. The device of claim 15 wherein said device is a soft contact lens.

21. The device of claim 20 further comprising an antibiotic or $Ag^+$ ionically bound or a quinolone or fluoroquinolone covalently bound to said aminopolycarboxylic acid or to the coupling agent at a total amount of less than one pre-determined systemic dose.

22. A polymeric device for use in medical applications, said device comprising:
   a base material formed out of a polymeric material into desired shape;
   a coating covering at least one surface of said base material, said coating including:
      an aminopolycarboxylic acid;
      a coupling agent for directly linking said aminopolycarboxylic acid to at least one surface of said base material.

23. The device of claim 22 wherein said coupling agent is cyanuric chloride.

24. The device of claim 22 wherein said coupling agent is cyanogen bromide.

25. The device of claim 22 wherein said aminocarboxylic acid is selected from the group of diaminopropanol hydroxy acetic acid, iminodiacetic acid.

26. The device of claim 22 further comprising an antibiotic ionically bound to said aminopolycarboxylic acid at a total amount of less than one pre-determined systemic dose.

27. The device of claim 22 wherein said device is a contact lens.

28. The device of claim 22 wherein said device is a catheter.

* * * * *